United States Patent [19]

Peters et al.

[11] 4,270,527
[45] Jun. 2, 1981

[54] INFLATABLE TROUSER FOR MEDICAL USE

[75] Inventors: John R. Peters, Chicago; Warren G. Armstrong, Northbrook, both of Ill.

[73] Assignee: Armstrong Industries, Inc., Northbrook, Ill.

[21] Appl. No.: 65,094

[22] Filed: Aug. 9, 1979

[51] Int. Cl.³ ............................................... A61F 5/04
[52] U.S. Cl. ........................... 128/87 R; 128/DIG. 20
[58] Field of Search ................... 128/87 R, 89 R, 90, 128/133, 134, DIG. 20, 24 R; 2/DIG. 3

[56] References Cited

U.S. PATENT DOCUMENTS

| | | | |
|---|---|---|---|
| 1,916,789 | 7/1933 | Fordham | 128/DIG. 20 |
| 2,762,047 | 9/1956 | Flagg et al. | 2/2 |
| 2,871,849 | 2/1959 | Chatham et al. | 128/1 |
| 3,823,711 | 7/1974 | Hatton | 128/78 |
| 3,823,712 | 7/1974 | Morel | 128/87 R |
| 3,826,249 | 7/1974 | Lee et al. | 128/DIG. 20 X |
| 3,933,150 | 1/1976 | Kaplan et al. | 128/24 R |
| 3,955,565 | 5/1976 | Johnson, Jr. | 128/DIG. 20 X |
| 4,039,039 | 8/1977 | Gottfried | 128/87 R |
| 4,202,325 | 5/1980 | Vicari et al. | 128/24 R |

FOREIGN PATENT DOCUMENTS

| | | | |
|---|---|---|---|
| 835003 | 2/1970 | Canada | 128/DIG. 20 |
| 483111 | 4/1938 | United Kingdom | 128/DIG. 20 |

*Primary Examiner*—Stephen C. Pellegrino
*Attorney, Agent, or Firm*—Tilton, Fallon, Lungmus

[57] ABSTRACT

An improved medical anti-shock trouser is disclosed which has replaceable pneumatic bladders so arranged and constructed to allow inflation in use without objectionable perimetric retraction and separation between adjacent bladders. The trouser takes the form of a panel of flexible porous fabric having an abdominal section and a pair of leg sections, each of the sections having a double-walled portion defining a pocket therein. An inflatable bladder is disposed in each of the pockets and, in the disclosed embodiment, the bladders of the leg sections are disposed in limited overlapping relation with respect to the bladder of the abdominal section. Each bladder has a flexible perimetric side wall as well as flexible top and bottom walls. The generally rectangular outline of tne abdominal bladder may be interrupted by a longitudinal slit positioned to extend centrally along the lower back of a patient, and/or by a transverse or circumferential slit positioned to extend over the patient's abdomen when the trouser is worn. Such slits provide access for trocar or needle insertion into selected sites along the patient's abdomen or back without requiring even partial deflation or removal of the trouser and without danger of puncturing the inflated bladder.

16 Claims, 11 Drawing Figures

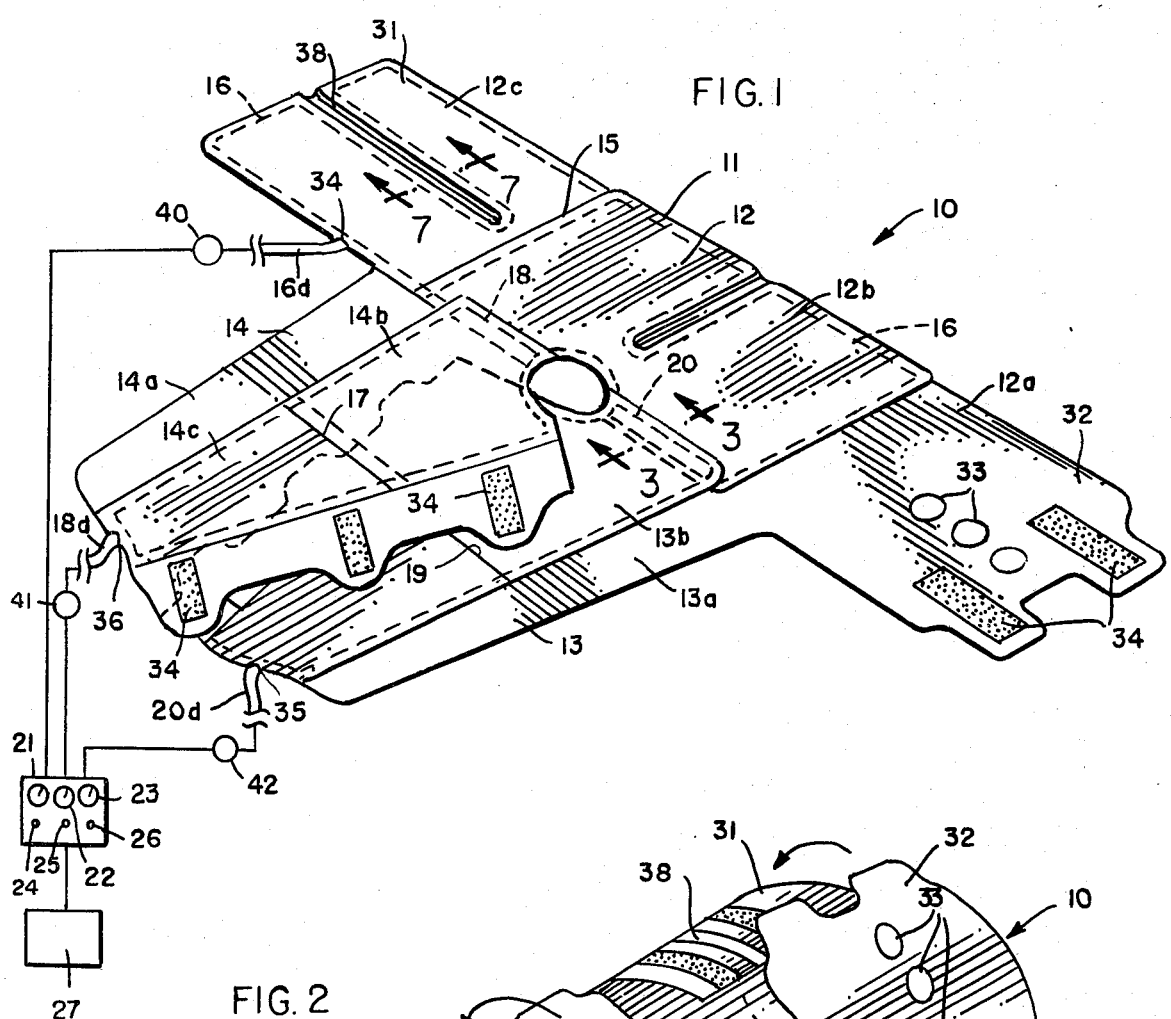
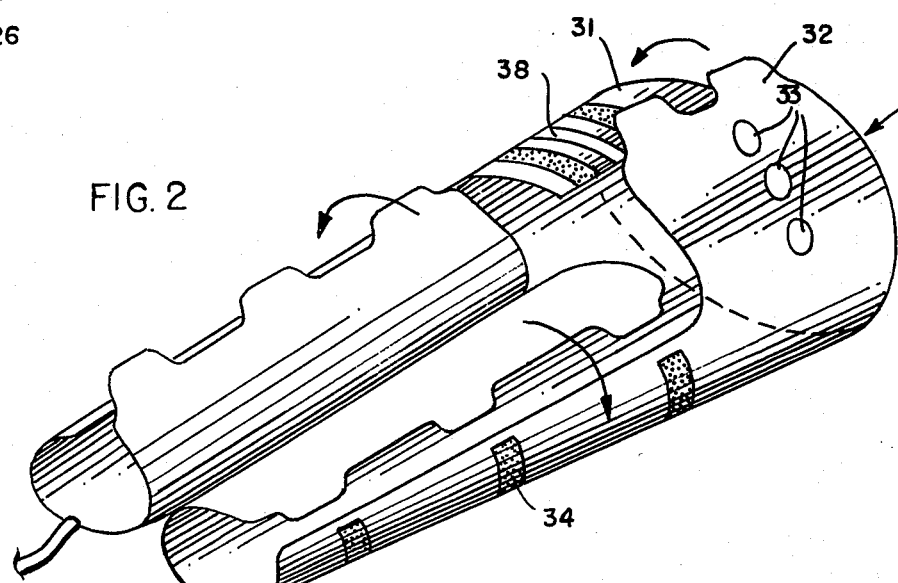
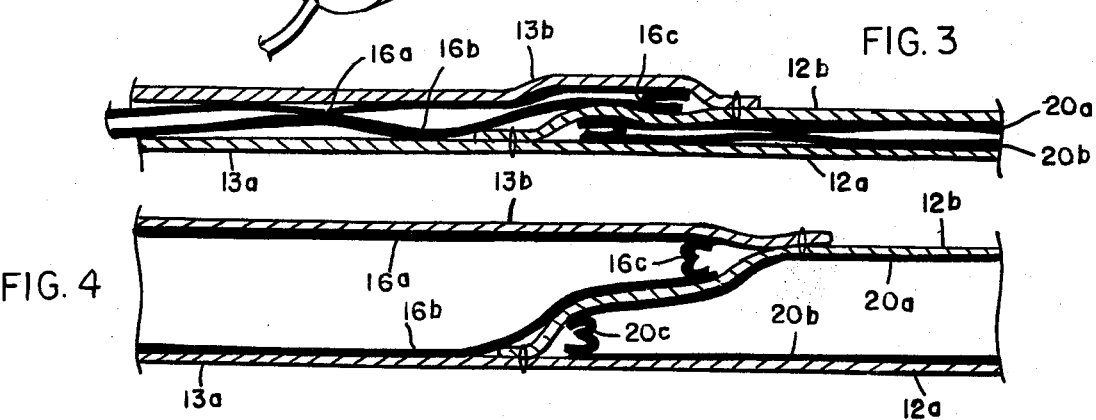

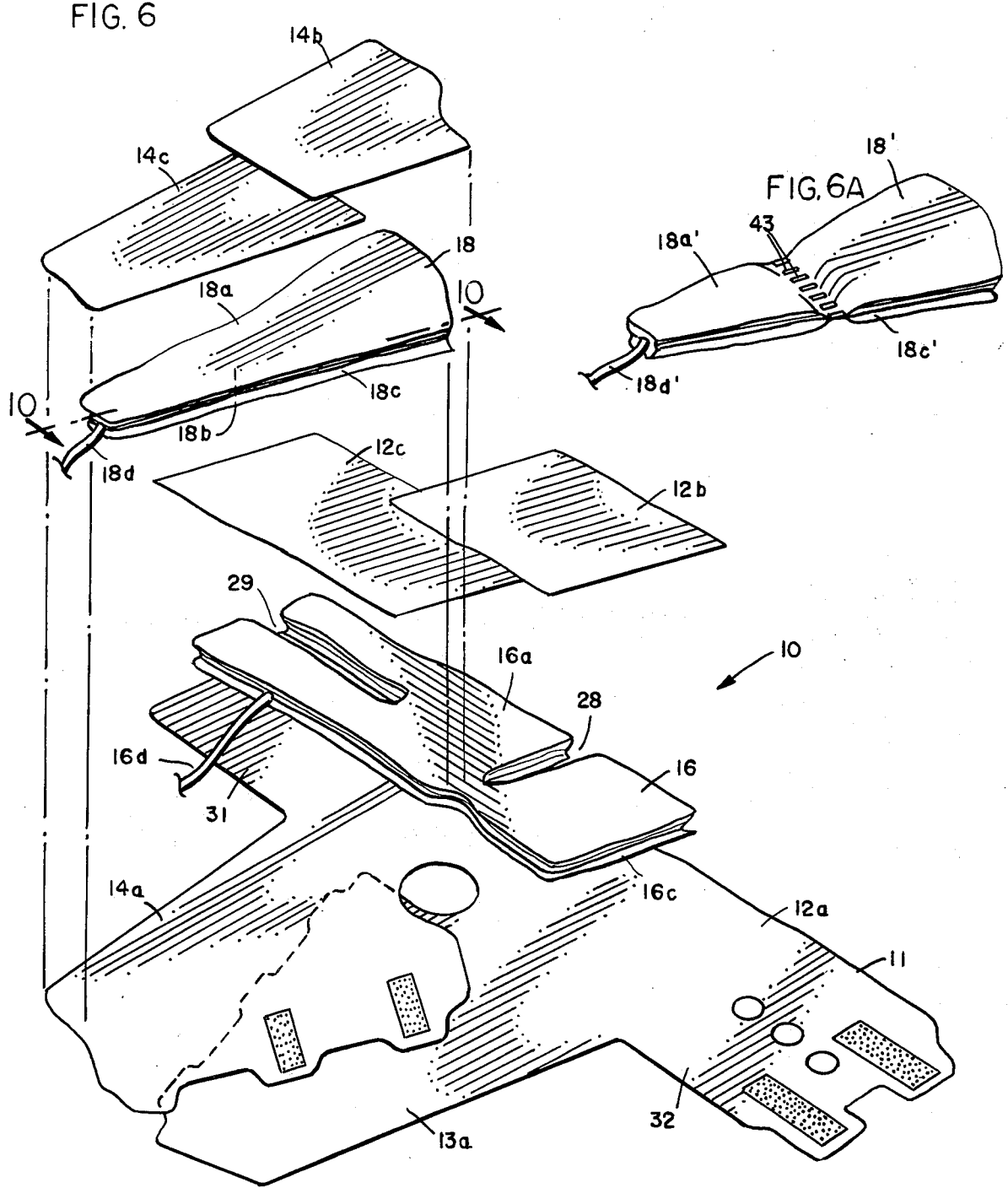

INFLATABLE TROUSER FOR MEDICAL USE

BACKGROUND

U.S. Pat. No. 3,933,150 discloses a medical anti-shock trouser, sometimes referred to in abbreviated form as a MAST suit, which is intended to be used in the emergency treatment of shock victims. The trouser takes the form of a double-walled panel having a pair of leg sections adapted to be wrapped about a patient's legs and an abdominal section to be wrapped about his abdomen. Between the impermeable walls of the panel is a chamber which may be inflated to apply circumferential counterpressure on the lower extremities and lower body section to decrease the volume of venous blood pooled therein, increase the circulation of blood to the patient's heart and brain, reduce hemorrhaging in the legs and lower body, and provide limited immobilization to protect the patient should there be fractures in the legs and lower body. While such MAST suits are widely used by emergency teams to help accident victims as they are being rescued and transported to medical facilities, it is believed apparent that their effectiveness is reduced if not completely destroyed, sometimes with fatal consequences for patients, should the chambers of such suits develop leaks during or prior to use. Unfortunately, should precautionary testing reveal that a suit has developed a leak, conventional suit design renders user repair of such a suit virtually impossible. The repair of leaks (which may be caused by organisms or general deterioration as well as by accidental puncture, overinflation, heat seal failure, etc.) generally requires factory attention and in many cases total replacement of the units. Unless an emergency team has at least one operative standby unit available, that team and the shock victims that it seeks to help must do without the benefit of a MAST suit while repair or replacement of a defective unit is being obtained.

Such problems have been reduced, but far from resolved, by providing each MAST suit with a plurality of inflatable chambers instead of only a single chamber. While it has been suggested (see U.S. Pat. No. 4,039,039) that the plural chambers need not be integral with the garment but might instead be located in pockets, such a construction does not appear to have ever become commercially available, possibly because of difficulties in achieving bladder removability and replaceability without interfering with the uniform application of pressure in use and, in general, without adversely affecting the operability and effectiveness of the structure as a whole.

A further problem with prior constructions relates to the difficulties of making abdominal punctures or spinal taps after the trousers have been fitted and inflated upon the patients. If, for example, a trouser must be partially or fully deflated in order to permit an abdominal puncture (usually to detect internal hemorrhaging), then such deflation may itself work to create the shock condition which the MAST suit is intended to protect against.

Other references revealing the state of the art are U.S. Pat. Nos. 2,762,047, 2,871,849, 3,823,711, 3,823,712, 1,916,789, Canadian Pat. No. 835,003, and Pelligra, R., and E. C. Sandberg, Control of Intractable Abdominal Bleeding by External Counterpressure, JAMA 241:708-713 (1979).

SUMMARY

One aspect of this invention lies in providing an improved anti-shock trouser which overcomes the aforementioned defects and disadvantages of prior constructions. Specifically, it is an object to provide a trouser which has a plurality of bladders, each of which may be easily removed and replaced. The advantages of providing multiple bladders is not offset by the disadvantages of having such bladders draw away from each other, causing gaps that might interfere with proper operation of the trouser, because the construction and arrangement of such bladders prevents or substantially reduces such retraction and separation. In addition, the construction of the abdominal bladder, and its relationship with the double-walled fabric panel which comprises a major element of the trouser, are such that when the trouser is in use selected areas are provided for the insertion of trocars or needles through the fabric thereof without requiring removal of the trouser or any change in its inflated condition. Such access areas for sample withdrawal (or for fluid injection) are provided at proper locations regardless of wide variations in the sizes of the patients upon which such a trouser may be fitted.

Briefly, the trouser comprises a panel of flexible porous fabric having an abdominal section adapted to be wrapped about the lower body or trunk of a patient and a pair of leg sections dimensioned to be wrapped about the legs of the patient. Each section has a double-walled portion and is provided with a bladder-receiving pocket. An inflatable bladder is dimensioned to be received within each of the pockets, each bladder having top, bottom, and perimetric side walls formed of tough, durable, and highly flexible polymeric material. When the bladder is collapsed, the side wall tends generally to fold inwardly between the top and bottom walls. As inflation occurs, the side wall thus tends to expand outwardly, permitting the top and bottom walls to move away from each other without appreciably reducing the outer dimensions or outline of the bladder.

Ideally, the pockets of the leg sections overlap the pockets of the abdominal section so that the bladders within such pockets are also in limited overlapping relation, whether such bladders are inflated or deflated. Such overlapping relationship between the bladders, especially when used as an adjunct to a bladder construction in which infolding side walls are provided, insures that inflation of the bladders in use will not cause separation or gapping between the bladder of the abdominal section and the bladders of the leg sections.

The bladder of the abdominal section is generally rectangular in outline and may have a slit or recess extending along the longitudinal midline of the garment to permit access for spinal fluid withdrawal, or possible fluid injection, when the trouser has been fitted and inflated upon a patient. The double fabric walls of the abdominal section may be joined together in the vicinity of such slit to delineate the area for needle insertion.

The abdominal section includes a pair of flaps which project laterally beyond the leg sections when the panel is in generally planar condition and which are wrapped in overlapping relation across the abdomen of the patient when the trouser is in use. The abdominal bladder extends into one of said flaps and may be provided with a slit or recess which extends inwardly in a transverse direction or, when the trouser is worn, in a generally circumferential direction across the patient's abdomen.

The fabric walls of the flap portion containing the recessed part of the abdominal bladder are preferably joined together within the area of the slit to delineate the zone through which an abdominal needle may be inserted. In addition, the other flap of the abdominal section, designed to overlie the first flap when the trouser is worn, is provided with windows or openings in register with the circumferentially elongated needle entry zone of the underlying flap. Preferably, a plurality of circumferentially-spaced windows are so provided to allow a doctor or paramedic to locate the desired site for needle or trocar insertion regardless of differences in patient girth.

In a modified form of the invention, the bladders of the leg sections may have their top and bottom walls sealed together at spaced points or lines in the vicinity of a wearer's knee, such sealed areas preventing the inflated bladders from interfering with knee flexure while at the same time allowing full inflation of those portions of the leg bladders above and below the wearer's knees.

Other features, objects, and advantages of the invention will become apparent from the specification and drawings.

DRAWINGS

FIG. 1 is a perspective view, shown partly diagrammatically, of an anti-shock trouser embodying the present invention.

FIG. 2 is a perspective view showing the trouser in the same orientation as in FIG. 1 but with the lateral portions of the leg and abdominal sections being folded into operative positions.

FIG. 3 is an enlarged and somewhat schematic fragmentary cross sectional view taken along line 3—3 of FIG. 1.

FIG. 4 is a sectional view similar to FIG. 3 but showing the relationship of parts when the bladders are inflated.

FIG. 6 is an exploded perspective view illustrating the relationship of parts when the trouser is generally oriented as shown in FIG. 1, the bladder and top (or inner) walls for the right-hand leg sections being omitted for clarity of illustration.

FIG. 6A is a perspective view of a modified leg section bladder which may be substituted for the leg section bladder of FIG. 6.

DETAILED DESCRIPTION

Figure 5:
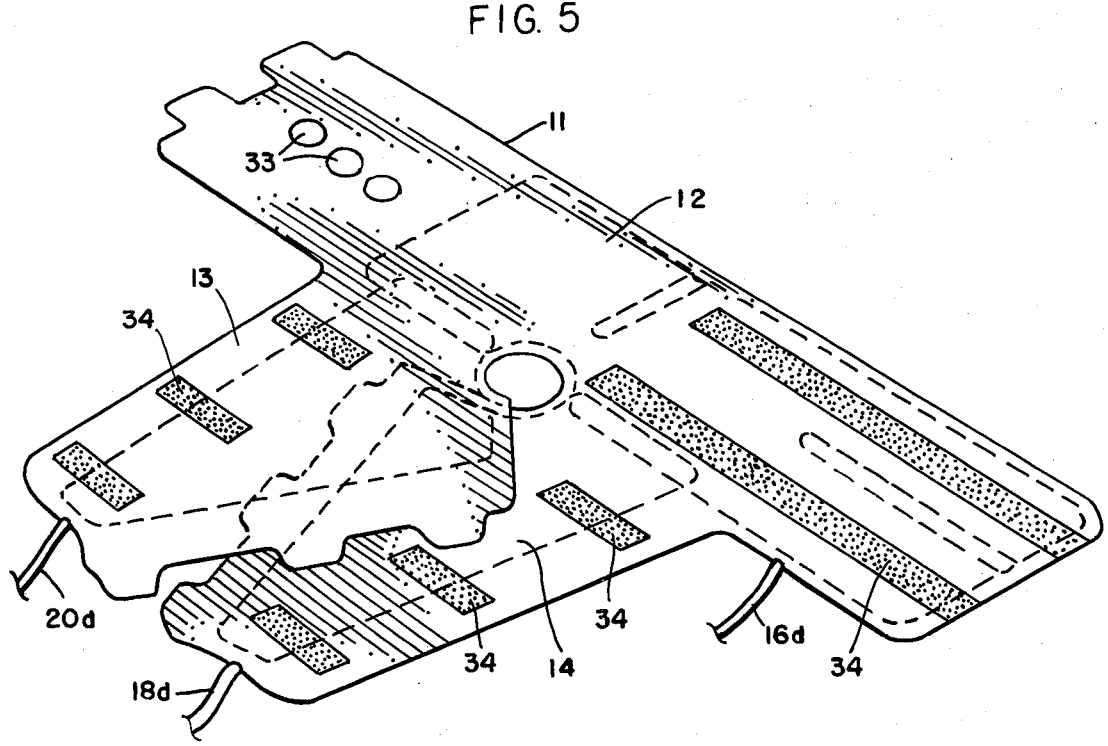
FIG. 5 is a perspective view similar to FIG. 1 but showing the trouser flipped over (from side-to-side) to reveal the normal undersurface thereof.

Referring to the drawings, the numeral 10 generally designates an anti-shock trouser embodying this invention. FIG. 1 shows the trouser in flattened or unfolded condition, as it would be laid out just before a patient is placed upon it, or just before it is slid beneath a patient, whereas FIG. 2 depicts the trouser as it would appear if a patient were being wrapped in it. The trouser takes the form of a panel 11 of flexible fabric, ideally a breathable or porous fabric (for example, denim) of natural or synthetic fibers, and includes an abdominal section 12 and leg sections 13 and 14. Each section has substantial areas of double thickness or double walls of fabric defining enlarged pockets for receiving inflatable bladders. Thus, the abdominal section 12 includes a bottom or outer wall portion 12a to which is secured, by peripheral stitching or other suitable means, a pair of upper or inner wall portions 12b and 12c. Between overlapping portions 12b and 12c of the upper wall is a slit-like opening 15 communicating with the pocket for the insertion and removal of abdominal bladder 16 (FIG. 6). If desired, one or more additional openings, preferably of similar construction, may be provided to facilitate insertion and removal of the bladder.

Similarly, each leg section 13 and 14 has a bottom or outer wall portion 13a and 14b, respectively, to which are secured upper or inner wall portions 13b, 13c, and 14b, 14c, respectively. Portion 14b overlaps 14c to define a slit-like opening 17 (more than one of which may be provided if desired) for the insertion and removal of leg bladder 18, and a similar relationship exists between portions 13b and 13c which overlap to define opening 19 for the insertion and removal of leg bladder 20.

All three bladders 16, 18, and 20 are formed of a highly flexible polymeric material. Any of a variety of tough, pliable, non-porous materials, either natural or synthetic, may be used. A thermoplastic material such as polyurethane is preferred. Each bladder is dimensioned to fit closely within the confines of its pockets and, as shown most clearly in FIGS. 3, 4, 6, and 10, has not only a top and bottom wall but also a perimetric side wall. More specifically, the abdominal bladder 16 has top and bottom walls 16a and 16b joined by perimetric side wall 16c, whereas the respective leg bladders 18 and 20 have top walls 18a, 20a, bottom walls 18b, 20b, and perimetric side walls 18c, 20c.

Each of the bladders is provided with a flexible tube 16d, 18d, and 20d extending to gauges 21–23, and to needle valves 24–26, for indicating the inflation pressure thereof and for deflating the bladders when the trouser is no longer in use. Such tubes may extend through the slits 15, 17, and 19 or, as shown in the drawings, through small openings 34, 35, and 36 especially formed for that purpose between the double walls of panel 11. A source of pressurized air 27 is connected to all three lines 16d, 18d, and 20d for inflating the bladders (FIG. 1). The pressure source 27 may take the form of a manually-operated air pump, a small power-operated compressor, a pressurized gas cartridge, or any other suitable inflating means. If desired, each of the lines 16d, 18d, and 20d may also be provided with separable couplings 40, 41, and 42 of conventional construction, equipped with automatic or manual closure means and disposed in close proximity to the respective bladders, to facilitate selective inflation, deflation, connection, or disconnection of each bladder.

Figure 10:
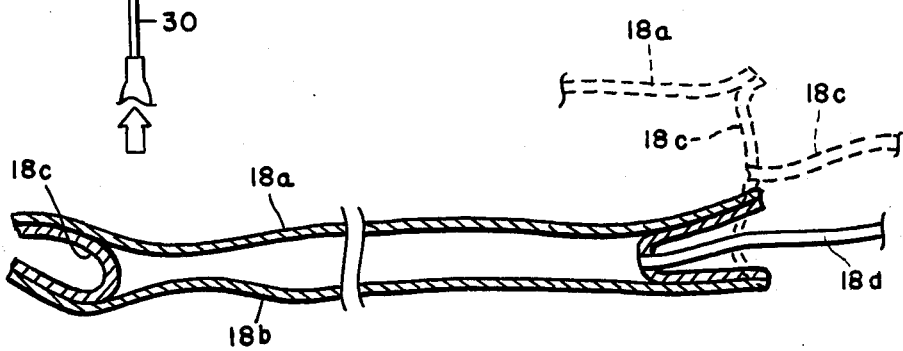
FIG. 10 is a sectional view of a leg bladder taken along line 10—10 of FIG. 6.

Referring to FIG. 10, which depicts leg bladder 18 as being representative of the basic construction for all bladders used herein, it will be observed that the perimetric side wall 18c tends to fold inwardly when the bladder is deflated. Upon inflation of the bladder, the top and bottom walls 18a and 18b spread apart and side wall 18c unfolds outwardly to assume the slightly outwardly bulging condition indicated by broken lines in FIG. 10. Unlike a standard pillow-shaped bladder, in which the top and bottom walls are joined directly to each other without an intermediate perimetric side wall, the bladder structure of FIG. 10 is capable of being inflated and deflated without appreciable dimensional changes in its outline. In other words, inflation is not accompanied by planar retraction, or at least significant planar retraction, of the bladder.

In the embodiment illustrated, a limited overlap is provided between the leg bladders and the abdominal bladder in order to completely eliminate the possibility of the formation of gaps between such bladders when they are inflated. FIG. 3 shows that the top wall portion 13b of the leg section 13 extends over, and is secured directly to, the top wall portion 12b of the abdominal section. Because of such overlapping relation between walls 13b and 12b, the pockets defined by the respective sections, and the bladders 16 and 20 within those pockets, also overlap. Such overlapping relationship is maintained even when the respective bladders are inflated, as indicated in FIG. 4. Therefore, although multiple bladders are provided, the effect upon the patient is essentially the same as if there were only a single bladder running the full length of the trouser.

Although the abdominal bladder is of generally rectangular outline (FIG. 6), a slit or recess 28 is provided which extends a limited distance along the longitudinal midline of the trouser. A similar slit or recess 29 extends transversely or, when the trouser is fitted about a patient, circumferentially. The two slits 28 and 29 provide access to the lower spinal area and abdominal area of the patient for the taking of fluid samples by means of suitable needles or trocars, or possibly for introducing fluids in the body by such means, without deflating, adjusting, or otherwise changing the condition of the inflated trouser.

Figure 7:
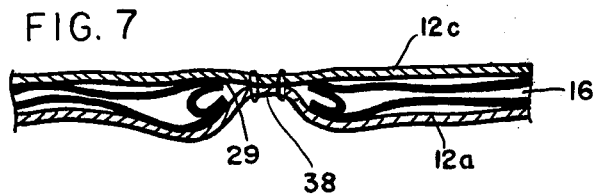
FIG. 7 is an enlarged fragmentary sectional view taken along line 7—7 of FIG. 1.
Figure 8:
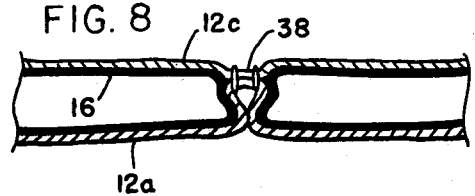
FIG. 8 is an enlarged fragmentary and somewhat schematic sectional view similar to FIG. 7 but illustrating the relationship of parts when the abdominal bladder is inflated.
Figure 9:
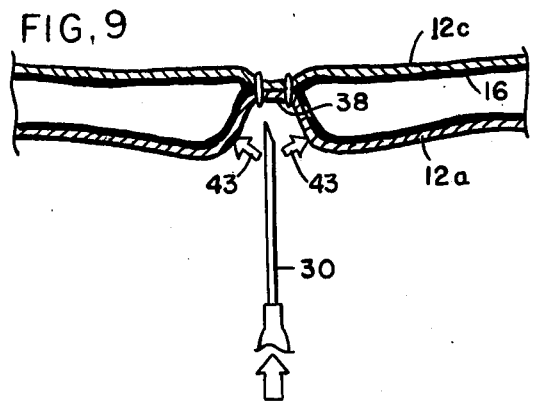
FIG. 9 is an enlarged fragmentary and somewhat schematic sectional view similar to FIG. 8 but showing limited displacement of portions of the trouser when an abdominal puncture is to be made.

Looking to FIGS. 1 and 7, top wall 12c and bottom wall 12a of the abdominal section are shown to be secured together by stitching or other suitable means within the slit or recess 29 of the abdominal bladder. The top and bottom layers 12b and 12a, respectively, are similarly joined together within longitudinal slit or recess 28. The secured areas therefore sharply delineate the zones 37 and 38 through which sampling needles may be inserted without risk of puncturing the abdominal bladder. When the abdominal bladder is inflated (and with the trouser fitted upon a patient), the access zones 38 and 37 tend to be concealed, the adjacent portions of the bladder expanding into such zones to help provide a more uniform application of pressure to the patient across such zones (FIG. 8); however, by means of any suitable retractor or other tool, or even by using the fingers, forces may be applied in the direction of arrows 43 (FIG. 9) to spread adjacent portions of the bladder and thereby expose such zone of interconnection. A needle or trocar 30 may readily be passed through the area of interconnection 38 (or 37) between the inflated portions of the abdominal bladder 16 for fluid withdrawal or injection.

The abdominal section 11 of the trouser is substantially wider than the overlapping leg sections, having laterally projecting flap portions 31 and 32 which are disposed in overlapping relation when the trouser is fitted about a patient (FIG. 2). Windows or openings 33 are provided in the outer flap portion 32, such windows extending over the circumferentially-elongated recess 29 of the abdominal bladder, and the zone of connection 38 between walls 12a and 12c within that recess, so that a doctor or paramedic may readily locate the proper site for needle insertion. Because of the circumferential elongation of recess 29 and the plurality of openings 33, the appropriate site for needle insertion may be found even though the trouser is fitted upon patients of substantially different size.

Any suitable means may be provided for releasably securing the flap portions of the abdominal section, and the edge portions of the leg sections, in overlapping relation. Mating strips of Velcro, designated in the drawings by numeral 34, have been found particularly effective, but other appropriate attachment means may be used.

FIG. 6A depicts an alternative form of insertable leg bladder for use in those situations where the rigidifying effect, or "splint effect", produced by the inflation of bladder 18 is deemed unnecessary or undesirable. Unlike bladder 18, bladder 18' has its top and bottom walls secured together at a plurality of spaced points or lines 44 in the knee portion thereof. Although such points or lines of attachment do not prevent the flow of gas from one end of each bladder to the other, they do reduce the extent of inflation in the bladder's knee portion (i.e., in the portion of each bladder that would be disposed directly behind or beneath a patient's knee when the trouser is worn) to allow a patient to flex his knees even when such bladders are fully inflated. Such flexure may be important if, for example, the trouser is to be worn in surgery where the most advantageous position for a patient may be an upright sitting position (often the case in brain surgery), or in situations where a patient tends to black out when sitting upright.

While in the foregoing we have disclosed embodiments of the invention in considerable detail for purposes of illustration, it will be understood by those skilled in the art that many of these details may be varied without departing from the spirit and scope of the invention.

We claim:

1. An inflatable trouser for medical use, comprising a panel of flexible material having an abdominal section and a pair of leg sections, each of said sections having double walls defining a pocket therein, and an inflatable bladder disposed in each of said pockets, wherein the improvement comprises said pockets of said leg sections and the pocket of said abdominal section being disposed in limited overlapping relation with portions of said walls separating the interior of the pocket of said abdominal section from the interiors of the pockets of said leg sections, and said bladders within said pockets of said leg sections being disposed in limited overlapping relation with respect to the bladder in the pocket of said abdominal section.

2. The trouser of claim 1 in which each said bladder has flexible top, bottom, and perimetric side walls.

3. The trouser of claim 2 in which said perimetric side wall of each bladder has outwardly-turned peripheral portions with surfaces thereof sealed in parallel relation to each of said top and bottom walls, whereby, said perimetric side wall of each bladder is predisposed to fold inwardly along a substantial portion of its length upon deflation of the bladder.

4. The trouser of claim 3 in which a flexible inflation-deflation tube is joined to each bladder at a point along the perimetric side wall thereof.

5. The trouser of claim 1 in which said flexible material of said panel is a porous fabric.

6. An inflatable trouser for medical use, comprising a panel of flexible material having an abdominal section and a pair of leg sections, each of said sections having double walls defining a pocket therein, and an inflatable bladder disposed in each of said pockets, wherein the improvement comprises said pockets of said leg sections and the pocket of said abdominal section being disposed in limited overlapping relation, and said bladders within said pockets of said leg sections being disposed in limited overlapping relation with respect to the bladder in the pocket of said abdominal section, said abdominal bladder being provided with an indentation in the outline thereof defining an elongated access slit, said indentation extending along that portion of said panel adapted to lie along the lower spinal column of a patient when said trouser is worn, said double walls of said abdominal section being secured together within said slit to define a zone for spinal needle insertion.

7. An inflatable trouser for medical use, comprising a panel of flexible material having an abdominal section and a pair of leg sections, each of said sections having double walls defining a pocket therein, and an inflatable bladder disposed in each of said pockets, wherein the improvement comprises said pockets of said leg sections and the pocket of said abdominal section being disposed in limited overlapping relation, and said bladders within said pockets of said leg sections being disposed in limited overlapping relation with respect to the bladder in the pocket of said abdominal section, said abdominal section including inner and outer flap portions adapted to be releasably secured together in overlapping relation across the abdomen of a patient, said abdominal bladder extending into said inner flap portion and being provided with an indentation in the outline thereof defining an elongated slit oriented to extend in a circumferential direction across a major portion of a patient's abdomen when said trouser is worn, said double walls of said abdominal section being secured together within said slit to define a zone for abdominal puncture.

8. The trouser of claim 7 in which said outer flap portion is provided with a plurality of circumferentially-spaced windows overlying said zone for abdominal puncture.

9. An inflatable trouser for medical use, comprising a panel of flexible material having an abdominal section and a pair of leg sections, each of said sections having double walls defining a pocket therein, and an inflatable bladder disposed in each of said pockets, wherein the improvement comprises said pockets of said leg sections and the pocket of said abdominal section being disposed in limited overlapping relation, and said bladders within said pockets of said leg sections being disposed in limited overlapping relation with respect to the bladder in the pocket of said abdominal section, each of said bladders having flexible top, bottom, and perimetric side walls, said bladder for each leg section having its top and bottom walls sealed together along spaced points positioned to underlie the knees of a wearer for defining a zone of flexure of said bladder when the same is inflated, said points of sealing between said top and bottom walls defining spaces therebetween for the flow of air throughout the chamber of such bladder.

10. An inflatable trouser for medical use, comprising a panel of flexible material having an abdominal section and a pair of leg sections, each of said sections being double-walled and defining a pocket therein, and inflatable bladders disposed in the respective pockets, said bladders each having flexible top, bottom, and perimetric side walls, said perimetric side wall of each bladder having outwardly-turned peripheral portions with surfaces thereof sealed in parallel relation to each of said top and bottom walls, whereby, said perimetric side wall of each bladder is predisposed to fold inwardly a substantial portion of the length thereof when the bladder is in deflated condition.

11. The trouser of claim 10 in which a flexible inflation-deflation tube is joined to each bladder for inflation and deflation thereof, said tube being joined to each such bladder along the perimetric side wall thereof.

12. The trouser of claim 10 in which said pockets of said leg sections and said pocket of said abdominal section are disposed in overlapping relation, and said bladders within said pockets of said leg sections and said abdominal section are also disposed in overlapping relation with respect to each other with portions of said walls of said sections separating the overlapping bladders within said overlapping pockets.

13. An inflatable trouser for medical use, comprising a panel of flexible material having an abdominal section and a pair of leg sections, each of said sections being double-walled and defining a pocket therein, and inflatable bladders disposed in the respective pockets, said bladders each having flexible top, bottom, and perimetric side walls, said perimetric side wall of each bladder being adapted to fold inwardly a substantial portion of the length thereof when the bladder is in deflated condition, said bladder within said abdominal section being provided with an elongated recess adapted to extend along the lower spinal column of a patient when said trouser is worn, said double walls of said abdominal section being joined together within said recess to define a zone for spinal needle insertion.

14. An inflatable trouser for medical use, comprising a panel of flexible material having an abdominal section and a pair of leg sections, each of said sections being double-walled and defining a pocket therein, and inflatable bladders disposed in the respective pockets, said bladders each having flexible top, bottom, and perimetric side walls, said perimetric side wall of each bladder being adapted to fold inwardly a substantial portion of the length thereof when the bladder is in deflated condition, said abdominal section including a pair of lateral flap portions adapted to be secured together over the abdomen of a patient with one of said flap portions overlying the other of said flap portions, said abdominal bladder extending into said other of said flap portions and being provided with an elongated recess adapted to extend in a circumferential direction over a major portion of a patient's abdomen when said trouser is worn, said double walls of said abdominal section being joined together within said recess to delineate a zone for abdominal needle insertion.

15. The trouser of claim 14 in which said one flap portion is provided with a plurality of windows arranged in a circumferentially-spaced series in register with said zone for needle insertion when said one flap portion overlies said other flap portion.

16. An inflatable trouser for medical use, comprising a panel of flexible material having an abdominal section and a pair of leg sections, each of said sections being double-walled and defining a pocket therein, and inflatable bladders disposed in the respective pockets, said bladders each having flexible top, bottom, and perimetric side walls, said perimetric side wall of each bladder being adapted to fold inwardly a substantial portion of the length thereof when the bladder is in deflated condition, said bladder for each leg section having its top and bottom walls sealed together along spaced points positioned to overlie the knees of a wearer for defining a zone of flexure of said bladder when the same is inflated, said points of sealing between said top and bottom walls defining spaces therebetween for the flow of air throughout the chamber of such bladder.

* * * * *